United States Patent [19]

Wiita et al.

[11] Patent Number: 5,339,800

[45] Date of Patent: * Aug. 23, 1994

[54] LENS CLEANING MEANS FOR INVASIVE VIEWING MEDICAL INSTRUMENTS WITH ANTI-CONTAMINATION MEANS

[75] Inventors: Bruce E. Wiita, Palm Beach Gardens; J. Michael Teets, Hobe Sound; Gregory D. Wiita, Palm Beach Gardens, all of Fla.

[73] Assignee: Devmed Group Inc., Palm Beach Gardens, Fla.

[ * ] Notice: The portion of the term of this patent subsequent to May 24, 2011 has been disclaimed.

[21] Appl. No.: 14,436

[22] Filed: Feb. 5, 1993

Related U.S. Application Data

[63] Continuation-in-part of Ser. No. 943,315, Sep. 10, 1992.

[51] Int. Cl.⁵ .................................................. A61B 1/00
[52] U.S. Cl. .................................................. 128/4; 128/6
[58] Field of Search ........................................ 128/4, 6

[56] References Cited

U.S. PATENT DOCUMENTS 5,025,776 6/1991 Silverstein et al. .................. 128/4
5,198,894 3/1993 Hicks ................................ 128/4 X Primary Examiner—Richard J. Apley
Assistant Examiner—Beverly A. Meindl
Attorney, Agent, or Firm—Norman Friedland

[57] ABSTRACT

Means for preventing contamination of the surgical viewing instrument including a flexible bag mounted on the proximal end of a hollow double walled tubular elongated member concentrically mounted to a borescope or surgical viewing instrument where the space between the walls define a passage for flowing fluid to a cuff or vortex generator disposed at the distal end of the tubular member which defines a discretely configured discharge port for flowing fluid over a lens surface for cleansing and defogging purposes. The lens serves to prevent blood, body fluid and other contaminates from back flowing and contaminating the surgical viewing instrument. A two-piece locking handle may be used to lock the lens cleaning apparatus to the borescope. Another embodiment includes a flexible tube utilized with the cuff.

2 Claims, 9 Drawing Sheets

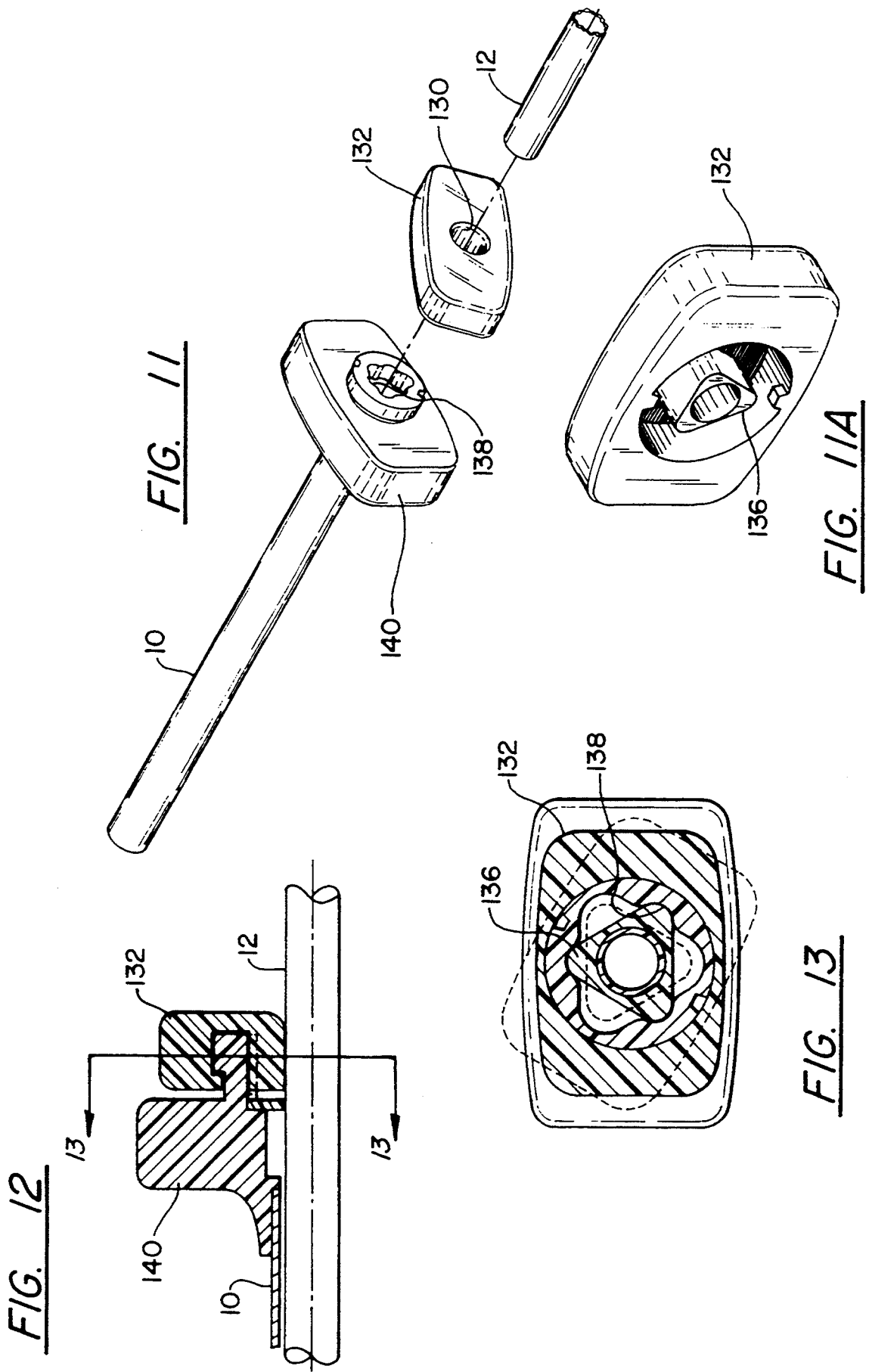

LENS CLEANING MEANS FOR INVASIVE VIEWING MEDICAL INSTRUMENTS WITH ANTI-CONTAMINATION MEANS

CROSS REFERENCE

This is a Continuation-in-part of our copending patent application Ser. No. 07/943,315 filed on Sep. 10, 1992 and entitled "Lens Cleaning Means for Invasive Viewing Medical Instruments".

TECHNICAL FIELD

This invention relates to biological viewing instruments that include a video camera or the like for internal viewing of the body and to means for cleansing and shielding the lens and particularly to means for isolating the camera to prevent contamination and obviate the need to resterilize before its next use.

BACKGROUND ART

There are a number of lens cleaning devices that are described in the prior art that are used on endoscopes, resectoscope, fiberscope catheterization devices and the like that provide for means for cleansing the lens. For example U.S. Pat. No. 4,770,163 granted to Oho et al on Sep. 13, 1988 and U.S. Pat. No. 4,576,146 granted to Kawazoe et al on Mar. 18, 1986 disclose apparatus for viewing blood vessels and the like by continuously flowing saline fluid through a passage formed in the endoscope at a flow rate that approximates the blood flow rate. Of particular interest is the lens cleaning means disclosed in these patents which show a pair of passageways that include outlets that flow the saline solution in front of the lens. The outlets serve to orient the flow so that the flow discharging from the outlets of each of these passageways oppose each other and hence, according to this patent, the interaction of the opposing fluids keeps the lens clean.

Also of interest as disclosed in the U.S. Pat. No. 4,576,146, supra, is the spiral passageway for injecting the saline solution with a spiral flow to displace the opaque liquid in the region of observation.

U.S. Pat. No. 4,690,140 granted to Mecca on Sep. 1, 1987 discloses an endoscopic tube with a passageway to route clear liquid to circulate around the endoscopic tube. Again this is another attempt to keep the lens clean.

U.S. Pat. No. 4,633,855 granted to Baba on Jan. 6, 1987 also discloses an endoscope that includes a tube mounted internally within the endoscope where the end at the distal end is bent approximately 90 degrees and directed toward the lens so as to blow air or water adjacent the observation window in order to keep it clean.

While these lens cleaning means may be satisfactory in certain biological procedures, they are not satisfactory for others. In the application of video-surgery in laporoscopic and arthroscopic procedures, for example, we have found that creating a film of cleaning fluid to form over the lens surface is a far more satisfactory method of keeping the lens clean or defogged, if it fogs up. In certain instances, injection of the fluid, which may be either water or carbon dioxide, intermittently as needed has proven to be a satisfactory method of keeping the lens clean and defogged.

This instrument employs a radial cavity with either partial or full circumferential flow directed over the surface of the lens or lens cover. In other embodiments this invention contemplates incorporating a vortex generator circumferentially mounted around the lens. This invention also contemplates incorporating a judiciously mounted fluid conveying passage integrated within the sheath surrounding the flexible types of medical instruments.

As is well known, it is time consuming and hence, expensive to have to sterilize the camera before each use. There is a need to re-use the camera for the next operation, but in heretofore scenarios, it is necessary to re-sterilize the camera before it is reused. To this end this invention contemplates means for isolating the camera and prevent contamination while providing means for the sanitary removal thereof, without the necessity of having to re-sterilize the camera again. This invention contemplates the use of a double walled tube that defines the passage for flowing the fluid medium being used for lens cleansing and a plastic lens laterally disposed in the passage for the fibre optics between the end of the cad, era and the lens cleansing means to isolate the camera from the cleansing fluid and any blood or body fluid or other contaminants from reaching the camera. A roll-up plastic bag is mounted at the end of the instrument and serves to follow the camera while it is being retrieved to encapsulate the entire camera and its attendant parts to keep it sterilized and to prevent it from becoming contaminated.

SUMMARY OF THE INVENTION

An object of this invention is to provide for a biological viewing instrument improved means for cleaning and/or shielding the lens with means for isolating the camera from contaminants.

A feature of this invention is to provide a double walled sheath concentrically surrounding the tube supporting the fibre optics that provide light and transmits the image to the camera (video or other types) used in video surgery that define a passage for flowing fluid to the discharge end that includes a radial channel with partial or full fluid flow capability formed in a cuff downstream of the lens and means to redirect the flow and coalesce the fluid and direct a film of fluid adjacent the surface and toward the center of the lens and a plastic disc laterally disposed in the passageway for the fibre optics to isolate the camera from contaminants.

Another feature of this invention is to provide at the distal end of the concentric sheath surrounding the medical tubular instrument used for biological observations a vortex generator circumferentially disposed relative to the lens of the instrument.

Another feature of this invention is to provide for a flexible medical instrument used for biological observation or video surgery a sheath fabricated from flexible material concentrically mounted relative to the instrument with a helical passage formed integrally with the sheath defining a channel for the passage of fluid.

Another feature of this invention is the incorporation of a two-part handle having the inner part connected to the lens cleaning apparatus and the upper part being rotatable relative to the lower part and each part having a camming arrangement for locking the lens carrying tube by a slight turn of the one handle relative to the other.

Another feature of this invention is to provide a double walled tube that defines the passage for conducting fluid to the lens cleansing means and inserting a plastic lens intermediate the end of the camera and the discharge end of the passage and providing a plastic bag attached to the proximal end of the instrument that is retracted in unison with the removal of the camera to "bag" the camera and keep it from becoming contaminated.

The foregoing and other features and advantages of the present invention will become more apparent from the following description and accompanying drawings.

BRIEF DESCRIPTION OF THE DRAWINGS

FIG. 3 is an enlarged sectional view of the end cap for securing the invention to an existing borescope, FIG. 5 is an enlarged view illustrating a vortex generator attachment, FIG. 8A is a partial view in section illustrating the rib portion for defining the helical flow path.

FIG. 11 is an exploded view in perspective illustrating the two-part locking handle;

FIG. 11A is a perspective view of the upper portion of the handle;

FIG. 12 is a partial view partly in section illustrating the two piece locking handle;

FIG. 13 is a sectional view, partly in phantom, taken along lines 13—13 illustrating the handle in the unlocked position;

BEST MODE FOR CARRYING OUT THE INVENTION

While in its preferred embodiment this invention is contemplated for use in video surgery, as for example for performing appendectomies, removal of gall bladders, removal of cancerous prostrate glands, and the like and for biological observation, it is to be understood that this invention has application in any environment where a lens is inserted into a cavity and ready access to cleanse the lens is not available. In a typical medical operation using video cameras the portion of the body to be observed is invaded by a Trocar which incises a small cylindrical hole through the body skin and tissue and is withdrawn leaving a hollow plastic tube in place. A tubular instrument (hereinafter referred to as a borescope) carries bundles of fiber optics which serves to transmit high intensity light beams to illuminate the area being treated and carries images back to the TV camera to view the sighted area. This invention is concerned with the lens that is located at the distal end of the borescope and particularly to means that cleanse and shield it and means for isolating the camera from the lens cleansing fluid, body blood and fluids and contaminates with the capability of sanitarily remove the camera and avoid the necessity of having to resterilize it in readiness for the next operation or use.

While the invention contemplates incorporating cleansing and shielding means to existing borescopes it is also within the scope of this invention to fabricate the borescope integrally with this invention.

Figure 1:
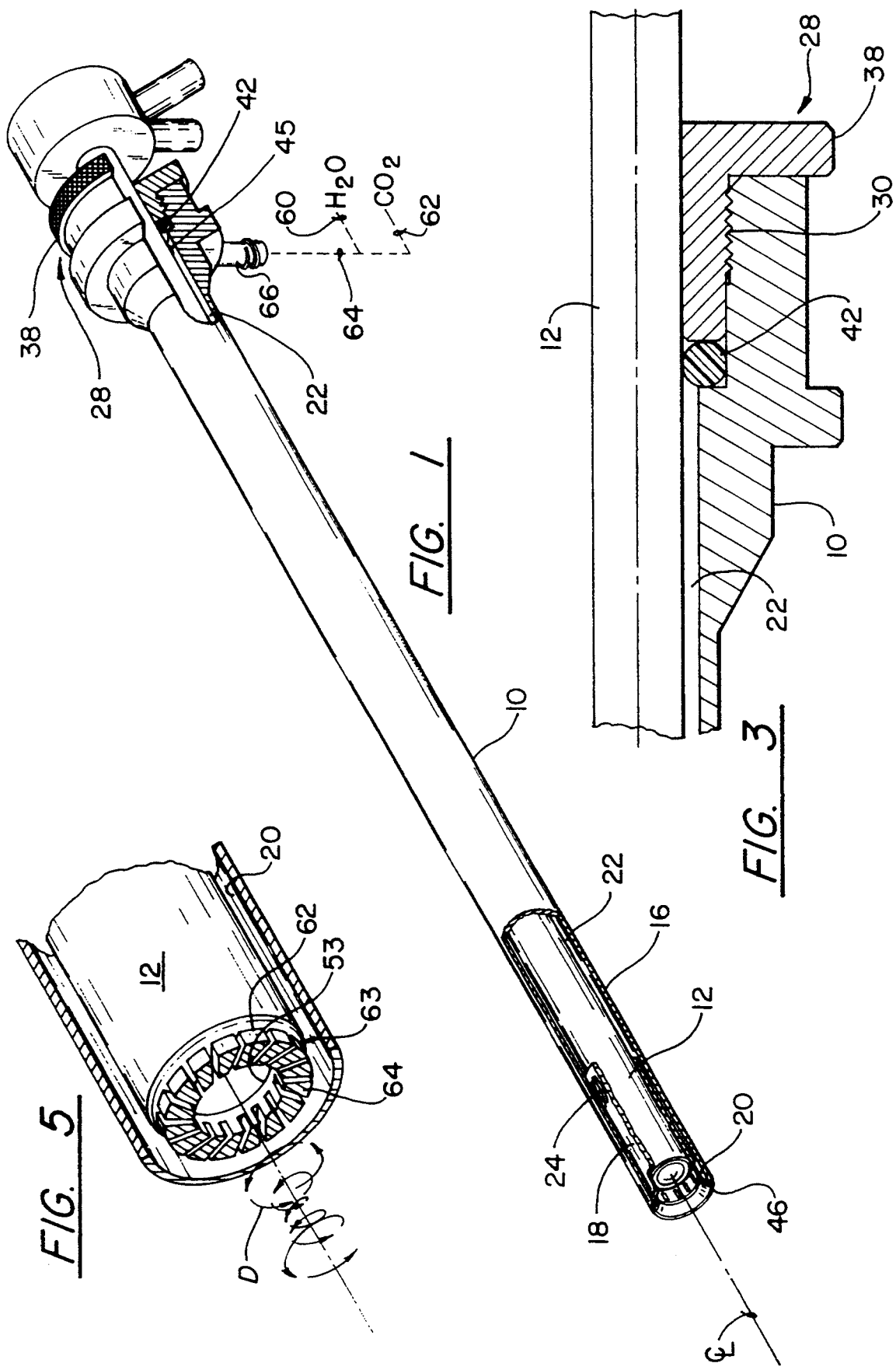
FIG. 1 is a perspective view partly in section illustrating the invention adapted to fit a borescope.
Figure 2:
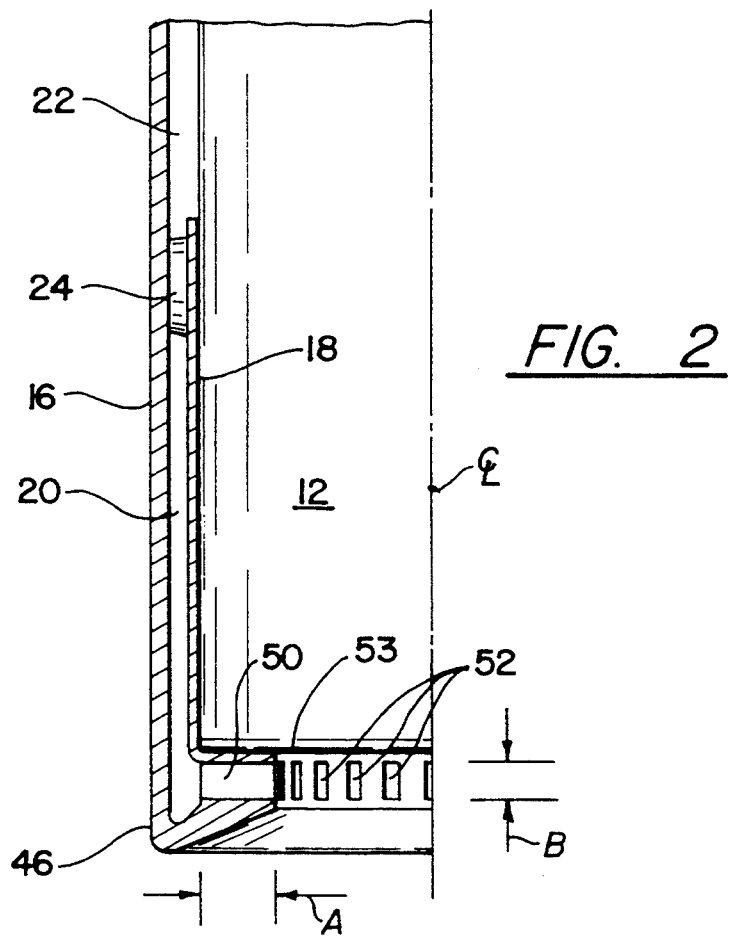
FIG. 2 is an enlarged partial view in section showing details of the lens cleaning passages of the embodiment shown in FIG. 1.

To best understand this invention reference is now made to FIGS. 1-3 depicting a hollow cylindrical tube 10 adapted to concentrically fit over the borescope 12. The diameter is selected to provide an annular space between the outside diameter of the borescope 12 and the inner diameter of the tube 10 having specific dimensions for the passage of sufficient fluid necessary for lens cleansing and shielding.

In one embodiment, the bottom or distal end is formed in two cylindrical pieces concentrically mounted relative to each other. The outer piece or sheath 16 extends the entire length of the tube and the inner piece is a short tube 18 mounted at the distal end and extends axially a short distance up the sheath 16. The diameter of the inner short tube 18 forms a snug fit with the outer surface of the borescope 12 and is slightly spaced to form the annular passage 20 that is in fluid communication with the annular passage 22 defined by the sheath 16. A plurality of spacers 24 are circumferentially spaced and extend between short tube 18 and the inner surface of sheath 16 and are suitably bonded thereto and serve to keep the two tubes in concentric alignment. It is contemplated that the short tube 18 be extended to define the double wall that will be described hereinbelow.

A retention nut and gland combination 28 threadably engages threads 30 formed on the inner diameter of sheath 16 at the proximal end and serves to secure and seal the sheath to the borescope. The outer circumference at the end of nut 38 may be knurled in order to manually torque the nut to the sheath. Sealing means, say O-ring seal 42, seals off the end to the passage 22.

Fluid is supplied to passage 22 through opening 45 formed in the sheath 16 and fluid such as water or carbon dioxide from a source (not shown) is regulated by suitable and commercially available valves, such as trumpet valves that are normally biased close and merely require depressing the valve stem to open, similar to those used in musical instruments.

The fluid in passages 22 and 20 is directed to a cuff 46 extending from and formed a part of sheath 16 that protrudes beyond the distal end of borescope 12. The passage 20 in cuff 46 includes a curved or flat bottom that serves to change the direction of the flow in passage 20. By virtue of the momentum of the flow the stream is directed to flow in the transverse passages 50 and discharge through the annular spaced outlets 52 and is directed toward the central axis of the lens. The stream of fluid is made to coalesce to form a film or sheet of fluid to flow over the outer surface of the lens cover 53. The dimensions of passage 50 and annular outlet are critical in that they are sized to give direction and coalesce the flow into a film which serves to clean the lens cover or lens directly if no cover is utilized. The dimensions of the length of the transverse passage 50 depicted by arrow A and the height of transverse passage 50 depicted by arrow B are critical and are selected so that the size of dimension A is substantially larger than the size of dimension B. In actual tests satisfactory results were obtained when the dimension of A was twice the dimension of B.

In operation suitable valves 60 or 62 (schematically shown) are activated to flow fluid through the line 64 coupled to fitting 66 which admits the fluid to annular passages 22 and 20 via the opening 45. The flow proceeds to the cuff 46 where it is guided by the bottom surface 47 and is forced to redirect the flow into the plurality of circumferential spaced passages 50. The flow discharging from the passages 50 are directed toward the central axes C of the borescope 12. The fluid may be preheated in order to accommodate the defogging feature.

Another advantage of the cuff 46 is that by virtue of the fact that it extends axially beyond the lens cover it serves to shield the lens from being in direct contact with body tissue and in fact creates a space between the outer edge of the cuff and the surface of the lens which allows the intensive light being transmitted by the fiber optics to diffuse in this space and maintain visibility.

As will be appreciated from the foregoing the outlet 52 is in a form of an annulus and is in proximity to the lens and in fact circumscribes the lens. This serves to attract, by capillary attraction, any liquid droplets that should remain on the lens after the liquid has been turned off. The attraction of the droplets is by a adhesion effect which has a tendency of drawing the liquid back toward the annulus and as a consequence the droplets are removed from the lens and thereby avoiding any distortion of the image being transmitted to the camera.

Figure 4:
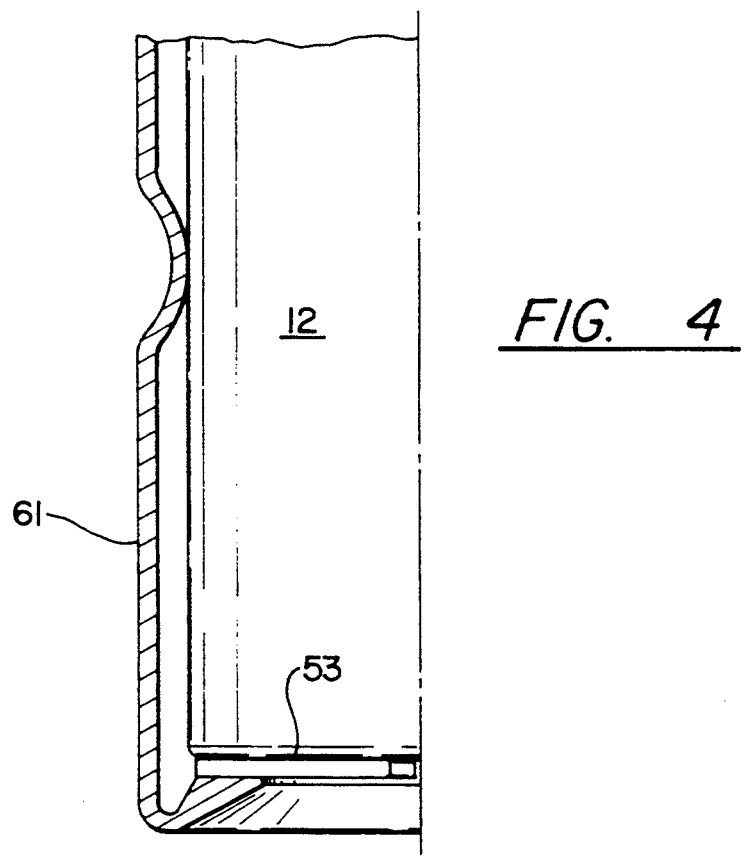
FIG. 4 is an enlarged partial sectional view illustrating another embodiment of this invention.

FIG. 4 depicts another embodiment where the number of outlets 52 are significantly reduced so that the span of the circumferential dimension is increased, simplifying the fabrication of the invention. Also the other sheath 61 is crimped at some distance up from the bottom end to form a dimple that bears against the outer circumferential surface of borescope 12 to keep the outer tube in concentric alignment. This replaces the spacers depicted in FIG. 1 to simplify the manufacture of the sheath. Obviously, the sheath 61 would be doubled-walled as will be described hereinbelow.

Instead of having the fluid discharge from the outlets 52 in a stream that is parallel or generally parallel to the lens cover, a vortex generator will be mounted at the outlet to impart a swirling motion to the fluid to in effect create vortices in front of the lens which will serve to not only clean the lens or its surface but also prevent loose tissue or other opaque substances from impinging on the lens. A suitable vortex generator generally indicated by reference numeral 63 is shown in FIG. 5. Generally the vortex generator is a ring-like member 62 that carries a pluralities of upstanding vanes 64 spaced around the circumference. Vanes 64 serve to impart a swirl to the fluid passing therebetween so that the fluid discharging from the vane defines a helical path depicted by the arrow D.

As is apparent from the foregoing the cleaning fluid that exits the channels defined between adjacent vanes 64 flows tangentially toward the center line C, across the lens and with a spiral motion the fluid then travels in an axial/radial direction outwardly over the face of cuff 46 and as a secondary cleaning function serves to prevent opaque fluids present in the body from migrating from the cuff to the lens. The swirling fluid serves to not only keep the lens clean or defogged but also creates a shield to protect the lens from loose matter in the area being viewed.

The components of the lens cleaning system can be fabricated from suitable and well known metallic or non-metallic materials.

Figure 6:
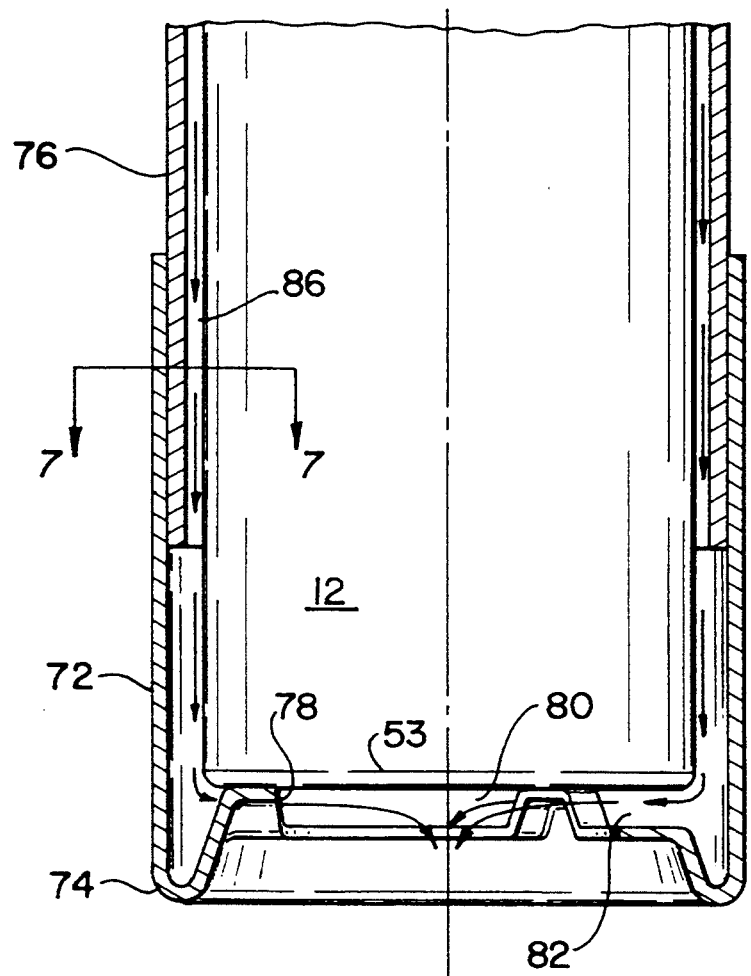
FIG. 6 is an enlarged partial sectional view illustrating another embodiment of this invention.
Figure 7:
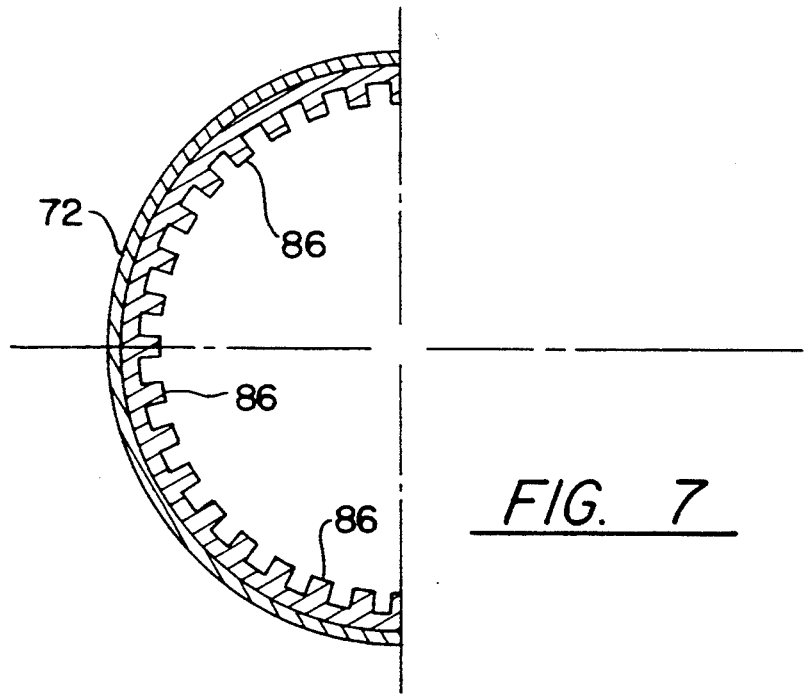
FIG. 7 is a partial view in section taken along lines 7—7 of FIG. 6.

FIGS. 6 and 7 exemplifies another embodiment where the short tube 72 defining cuff portion 74 is fabricated from sheet metal stock and is attached to the end of sheath 76 (similar to sheath 16 depicted in FIG. 1). The bottom end is crimped to define dimple 78. The lens cover 53 bears against the dimple 78 when installed and defines the space 80 to allow the flow discharging from the annular discharge 82 to flow over the surface of the lens. Similar to the embodiment depicted in FIG. 1, the cuff 74 serves to change the direction of the flow so that the flow passes beyond the lower extremity of the distal end of borescope 12 and is redirected to the outlet discharge end before being discharged adjacent the surface of the lens. In this embodiment of FIGS. 6 and 7 the tube 76 is held in concentric relationship with the borescope 12 by the scallops 86 formed on the inner diameter of tube 76.

Figure 8:
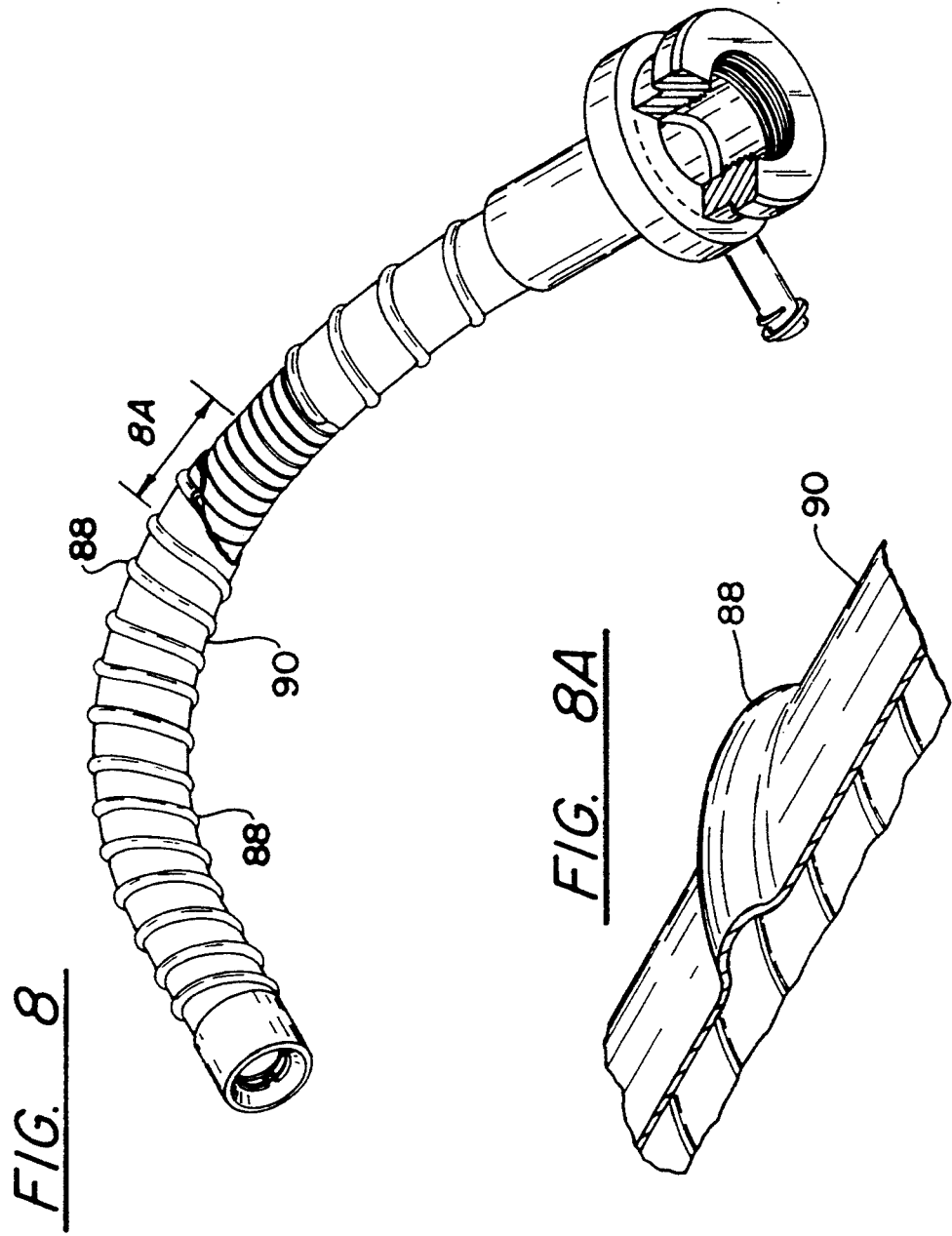
FIG. 8 is a view in perspective illustrating another embodiment of this invention when applied to a flexible borescope.

FIGS. 8 and 8A discloses the instrument for use when the borescope is formed from a flexible tube. In this embodiment a helical formed channel 88 is formed in the flexible tube 90 which may be fabricated similar to BX metal cable to define the passage for flowing the fluid from the inlet to the discharge end. The cuff portion which can be identical to the versions shown in FIGS. 1, 4, and 6 is secured to the end of the flexible tube 90. As seen in FIG. 8A the rib 88 defines a flexible helical channel to the borescope outside diameter for delivering the fluid from the proximal end to the distal end of the lens cleaning tubular member.

Figure 9:
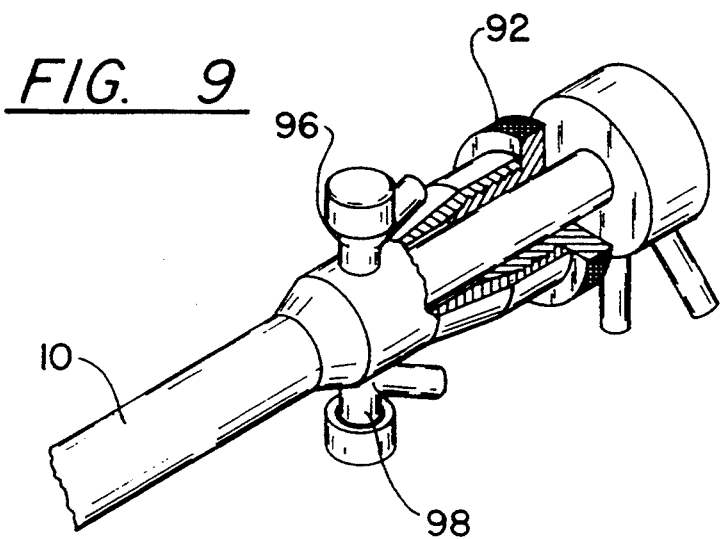
FIG. 9 is a partial view in perspective and partly in section illustrating a version of this invention employing a valving arrangement for controlling the cleansing and/or shielding fluids.
Figure 10:
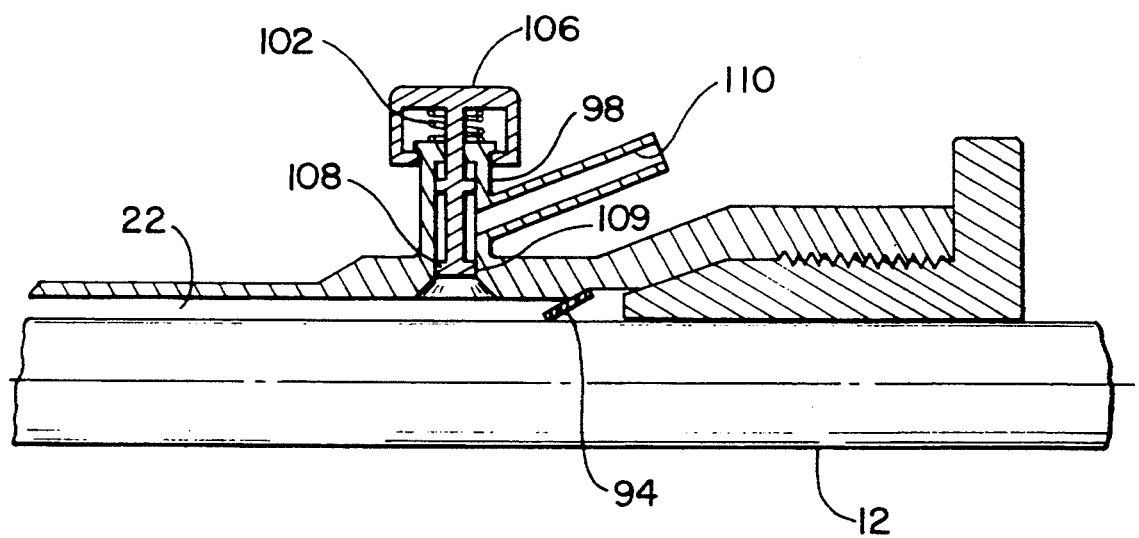
FIG. 10 is a partial view in section showing the details of the embodiment of FIG. 9.

FIGS. 9 and 10 illustrate optional attachment means and trumpet valve means that can be employed with this invention. In this embodiment the borescope 12 is inserted in the tube 10 and held in place by end cap and bolt 92 threaded to the end of tube 10. A packing or gland illustrated by reference numeral 94 seals the end of the borescope 12. Suitable trumpet valves 96 and 98 serve to admit the fluid desired. The trumpet valve as shown in FIG. 10 consists of a plunger 100 that is spring biased by coil spring 102 in the upward direction. Depressing button 106 positions valve element 108 away from seat 109 placing passage 110 in fluid communication with passage 22.

As can be seen in FIG. 11 and FIG. 12 a two-piece handle is provided to conveniently lock the tubular member 10 to the borescope 12. The borescope 12 is inserted in the central passage 130 and extends throughout the distal end. The upper handle 132 carries an elongated triangular shaped cam element 136 that extends into the aperture 138 formed in lower handle 140. Aperture 138 is configured to define detente that have a smaller diameter area than the diameter area of the aperture 138. Hence, by rotating the upper handle 132 relative to the lower handle 140, which is held in place by the operator with the use of his other hand, the apex of the triangular shaped cam 136 fits into the smaller diameter area detente and the material of cam 136 is sufficiently flexible and resilient to fictionally engage the outer diameter of the borescope 12 and lock it into place.

As will be appreciated by those skilled in this art another use of the lens cleansing apparatus is the ability to irrigate the surrounding area by injecting a stream of fluid in the area where the surgeon requires a better or clearer view. To accomplish irrigation the operator merely depresses the trumpet valve to allow a stream of fluid to be injected in the surrounding area and leaves the valve in the operative mode until the area is visible. The trumpet valve can include suitable means to hold the valve in the operative position.

FIGS. 14, 14A, 15, 16 and 17 exemplify another embodiment where the cleansing lens is adapted to permit the removal of the camera and its associated mechanism from being removed while preventing it from becoming contaminated and obviating the need to resterilize it. In accordance with this invention the tubular member 200 which fits over the fiber optics is formed from a double wall including the inner wall 202 and the outer wall 204 concentrically disposed in a unitary unit. As noted in FIG. 16, the spacer 201 serve to keep the inner wall 202 and outer wall 200 concentric. The spacer may be fabricated to extend the length of the double walled tubular member and the passages in this configuration will be arcuate slots. Obviously the double wall defines the annular passage 206 (or arcuate slotted passages) that conducts the cleansing fluid to the lens cleaning member 208, which may take the form of the structure disclosed in FIGS. 1 or 5. It will be noted that the inner wall 202 is slightly shorter than the outer wall and provides the lateral passage 210 to communicate with the cuff 212.

The transparent circular plastic member 214 is fitted at the bottom of the inner wall 202 and disposed just upstream of the lateral annular passage 210. This has a dual function 1) to permit viewing by the camera and 2) to seal off the borescope from body fluids and lens cleaning fluid. This keeps the camera and its attendant parts sterilized. The three tangs 216 on the circular plastic member are removed before mounting into the inner wall. Tangs 216 are used in the manufacturing of the circular member 214.

Figure 14:
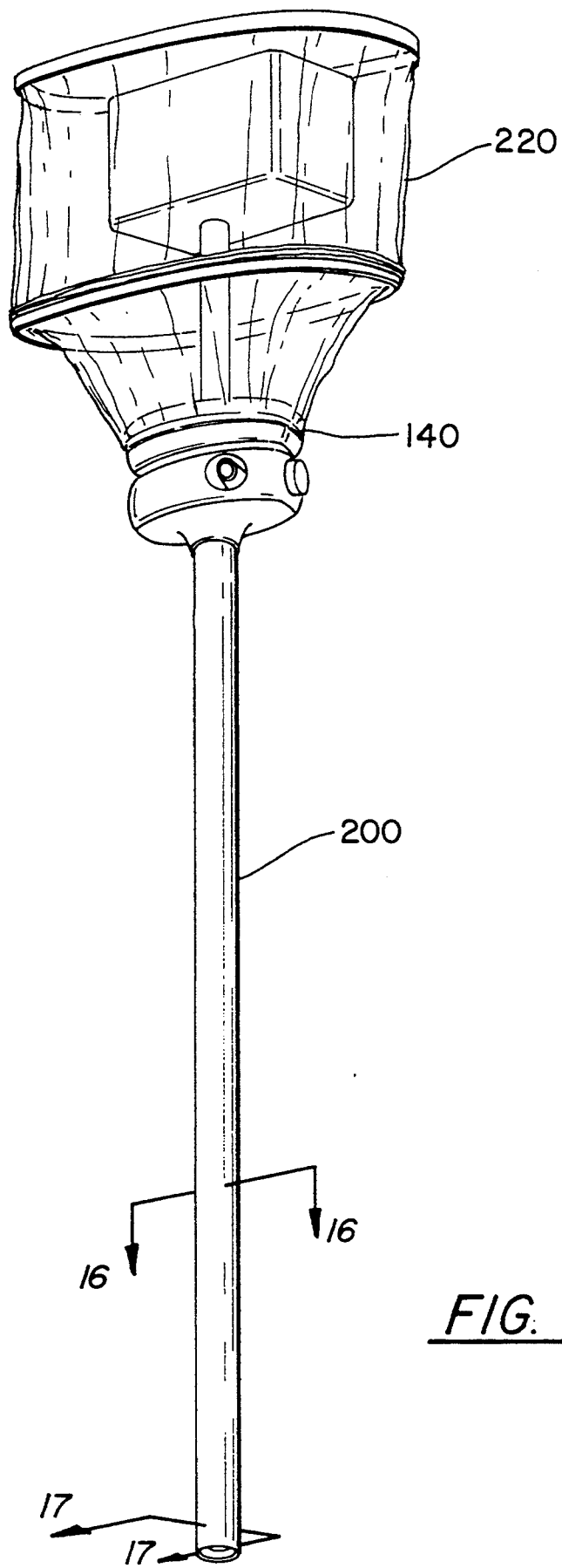
FIG. 14 is a view in elevation and phantom showing the plastic bag mounted to the instrument depicted in FIG. 11 and the camera.
Figure 14A:
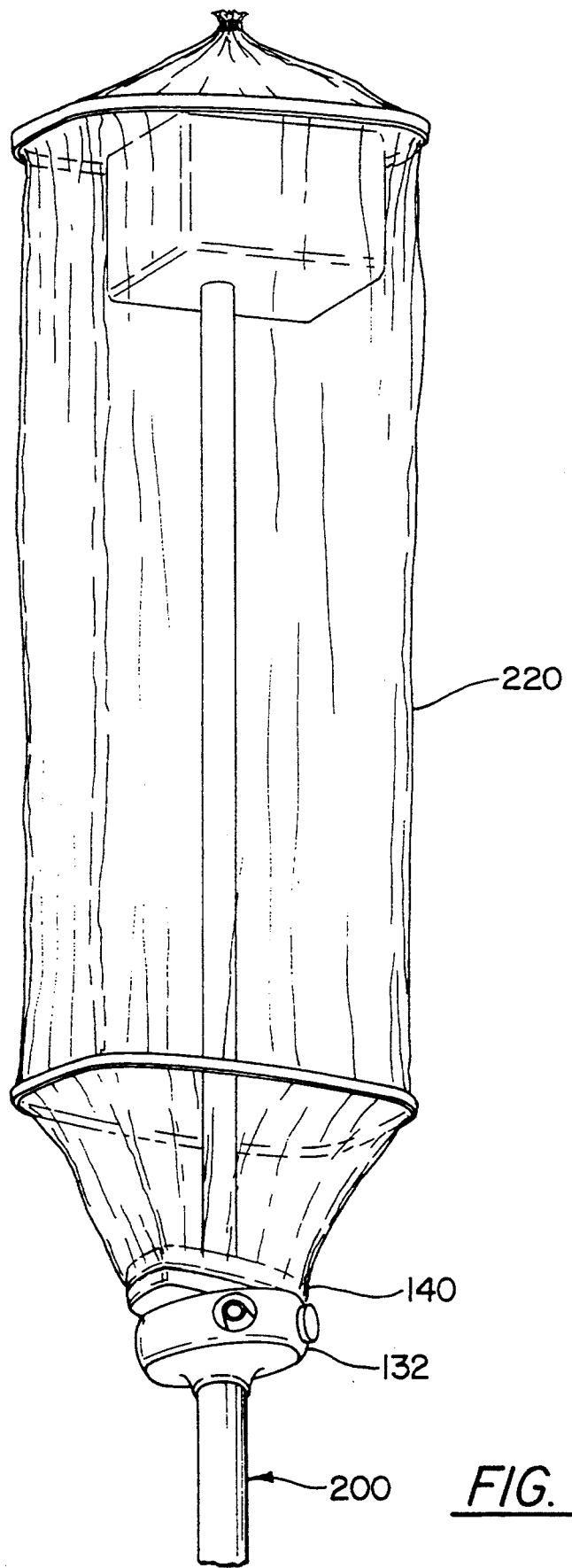
FIG. 14A is a view identical to the structure in FIG. 14 showing the camera being removed and the plastic bag being extended.
Figure 16:
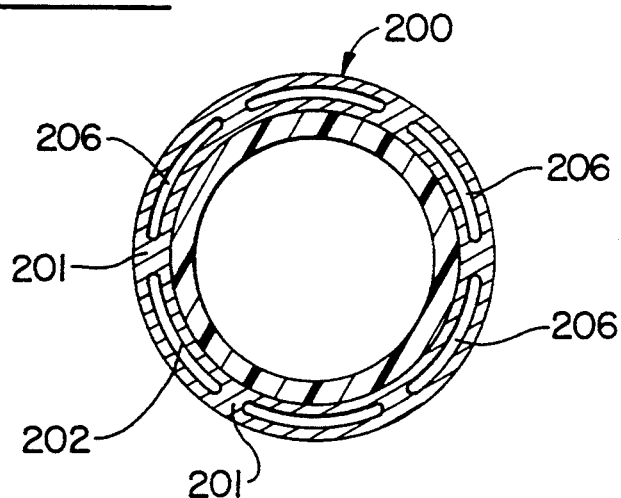
FIG. 16 is a section taken along lines 15—15 of FIG. 15.
Figure 15:
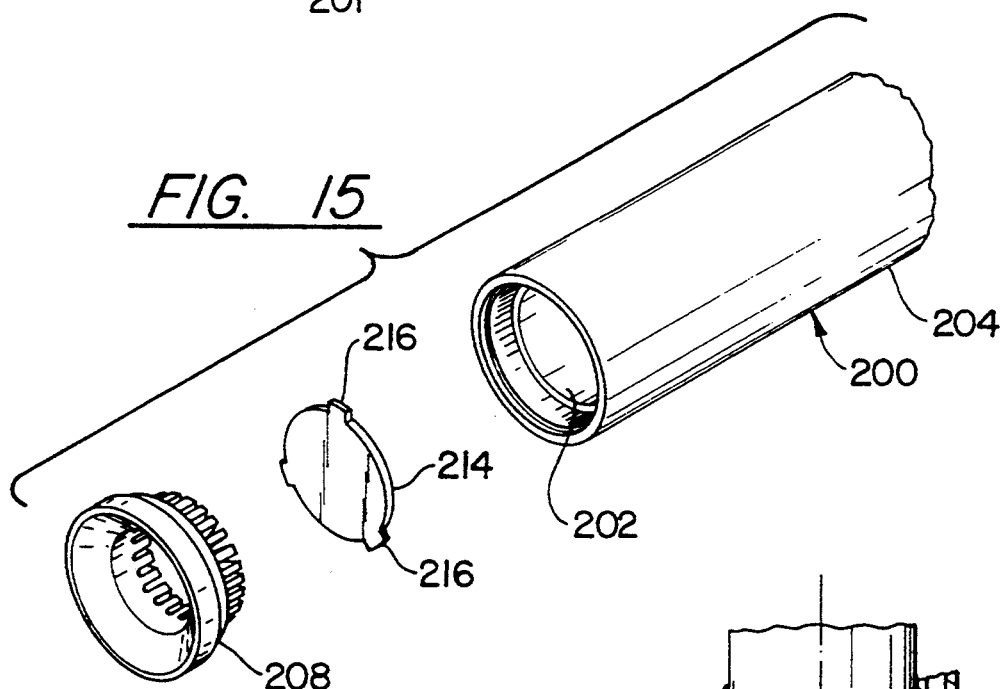
FIG. 15 is a partial exploded view showing the double walled tube and the plastic lens.
Figure 17:
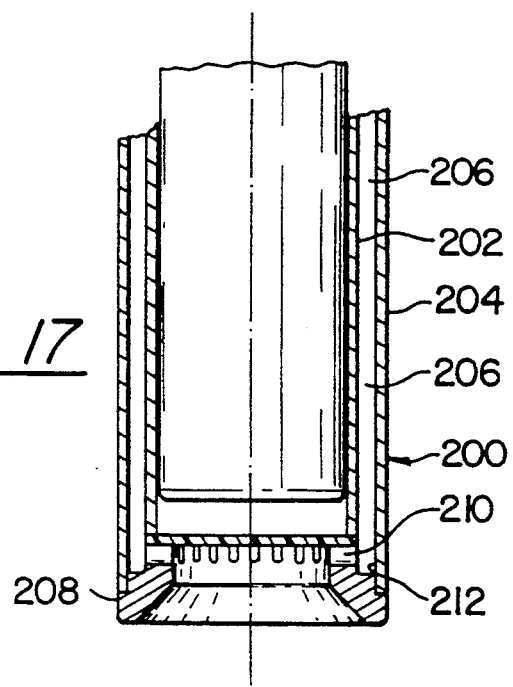
FIG. 17 is a partial sectional view taken along lines 17—17 of FIG. 14.

In accordance with this invention a plastic bag 220 is tied to the proximal end of the lens cleaning instrument and encapsulates the camera. The plastic bag is folded and nested in a well known manner and is commercially available and both ends can be tied closed. As shown in FIG. 14 A, the plastic bag unfolds and is extended to encapsulate the entire borescope. After the operation the camera is removed from the top end of the bag and slid out of the lens cleansing instrument. The bag attached to the lens cleansing instrument is either disposed of with the lens cleansing instrument or removed and disposed of. The lens cleansing instrument may be resterilized to be reused. However, since the camera and the attendant parts were prevented from becoming contaminated, the camera can be reused without the necessity of having to resterilize it before the next use.

Although this invention has been shown and described with respect to detailed embodiments thereof, it will be appreciated and understood by those skilled in the art that various changes in form and detail thereof may be made without departing from the spirit and scope of the claimed invention.

What is claimed:

1. Apparatus for cleansing the lens of a viewing camera used in biological observation by penetration into the cavity of living beings, the camera having an elongated tube housing fibre optics for producing a lighted area from a light source and a image relay for a television camera the improvement comprising:
    a double walled tubular member concentrically mounted around said elongated tube and including a longitudinal passageway defined between the inner wall and outer wall of said double walled tubular member,
    a lens extending laterally in said elongated tube disposed at the distal end to prevent the backflow of blood, body fluids and contaminants from reaching said fiber optics and said camera,
    a cuff portion extending beyond the distal end of said elongated tube to reduce lens contact with body parts to inhibit opaque fluids from obscuring visibility, said cuff portion including fluid passage means in fluid communication with said longitudinal passageway and defining at least one discharge port at the end of said elongated tube, said cuff portion including a bottom wall surface to redirecting the flow of fluid in said passage means to flow into said discharge port and flow laterally in a direction to scrub the surface of the lens mounted at the distal end of said elongated tube,
    said discharge port being sized to coalesce and direct the flow of fluid to form a sheet of fluid,
    means for admitting fluid into said elongated passage whereby the flow of fluid formed into a sheet is directed over the lens on demand of the operator; and
    bag means attached to the proximal end of said elongated tubular member to encapsulate said camera and fiber optics,
    means for generating a vortex of said fluid disposed at the end of said discharge port,
    said means for generating a vortex including a plurality of spaced vanes circumferentially spaced about an axis that is disposed coaxially relative to the longitudinal axis of said lens, and,
    cap means having an upper member and a lower member being in rotatable relationship, said lower member being affixed to the proximal end of said tubular member, a cam member having radially extending lobes and having a central passage adapted to fit over the proximal end of said elongated tube supported internally of said upper member, said lower member having a central opening in cooperating relationship relative to said cam and having detentes for receiving said lobes, said upper member and said lower member defining handle means so that engagement by an operator causes said upper member to rotate relative to said lower member for placing said lobes into said detentes for locking said elongated tube to said tubular member.

2. Apparatus for cleansing the lens of a viewing camera used in biological observation by penetration into the cavity of living beings, the camera having a flexible elongated tube housing fiber optics for producing a lighted area from a light source and a image relay for a television camera the improvement comprising:
    a flexible tubular member concentrically mounted around said elongated tube having a helically extending rib portion defining a helical passage, a cuff portion extending beyond the distal end of said elongated tube including fluid passage means in fluid communication with said helical passage and defining at least one discharge port at the end of said elongated tube, said cuff portion including a bottom wall surface for redirecting the flow of fluid in said passage means to flow into said discharge port and flow laterally in a direction to scrub the surface of the lens mounted at the distal end of said elongated tube, and bag means attached to the proximal end of said elongated tube to encapsulate said camera.

* * * * *